United States Patent [19]

Rokugawa

[11] Patent Number: 4,621,059
[45] Date of Patent: Nov. 4, 1986

[54] APPARATUS FOR MEASURING VELOCITY OF ENZYME REACTION

[75] Inventor: Kyuji Rokugawa, Ootawara, Japan

[73] Assignee: Kabushiki Kaisha Toshiba, Kawasaki, Japan

[21] Appl. No.: 708,509

[22] Filed: Mar. 5, 1985

[30] Foreign Application Priority Data

Mar. 5, 1984 [JP] Japan .................................. 59-40567

[51] Int. Cl.$^4$ ............................................. C12M 1/34
[52] U.S. Cl. .................................... 435/291; 356/417; 422/52
[58] Field of Search ................ 435/291; 356/436, 410, 356/411, 417; 250/361 C; 422/52

[56] References Cited

U.S. PATENT DOCUMENTS 3,413,464 11/1968 Kamentsky ...................... 356/410 X
4,021,307 5/1977 Mosbach ............................ 435/291 X
4,537,861 8/1985 Elings .............................. 356/417 X
4,563,331 1/1986 Losee ............................... 435/291 X Primary Examiner—Alan Cohan
Attorney, Agent, or Firm—Finnegan, Henderson, Farabow, Garrett & Dunner

[57] ABSTRACT

An enzyme is immobilized to a capillary column, and a solution which contains a chemical substance and a luminescent substance flows through the column. A plurality of optical fibers are arranged along the longitudinal direction of the column, and the luminescence in the column is introduced to a photodiode array through the fibers. The distribution of the luminescent intensity along the longitudinal direction of the column is detected by the photodiode array. Thus, the rate of quantity increase of the product produced by the enzyme reaction can be measured while the solution is flowing through the column, thereby producing the enzyme activity by the end assay and the rate assay.

11 Claims, 6 Drawing Figures

APPARATUS FOR MEASURING VELOCITY OF ENZYME REACTION

BACKGROUND OF THE INVENTION

The present invention relates to an apparatus for measuring the velocity of an enzyme reaction used for the activity measurement of an enzyme or the quantification of a chemical substance.

An enzyme acts as a catalyst in a chemical reaction. Such a chemical reaction is called "an enzyme reaction". The activity of the enzyme is the velocity of the enzyme reaction, the activity measurement of the enzyme is the catalytic function of the enzyme, i.e., to identify the effective quantity, and fundamentally has an important meaning in the case of handling the enzyme.

A process for measuring the activity of an enzyme heretofore or a process for measuring the quantity of a chemical substance in a specimen includes an electrochemical process and an optical process.

A process for electrochemically detecting the quantity of a substance produced or erased by an enzyme reaction using an immobilized enzyme in a column is known as the electrochemical process. In this process, the enzyme can last for a long time, and the enzyme reaction is stable. However, since a change in the quantity of chemical substance is detected at an outlet of the column, the process can detect the quantity only by an end assay but is improper for a rate assay.

Another known electrochemical process is to dip enzyme electrodes in a specimen. In this process, carriers immobilized with the enzyme are arranged at the enzyme electrodes. This process can perform a rate assay. However, it cannot measure the activity of the enzyme while continuously flowing a substrate solution, and it merely measures the activity of the enzyme by creating the enzyme reaction in a discrete or batch manner. Further, since it is necessary that the substance which increases or decreases in the immobilized enzyme diffuses in the carrier of the immobilized enzyme to reach the surface of the electrode in case of detecting the reaction substance, the responding time of the electrode depends upon the diffusing distance in the carrier. Therefore, it is necessary to reduce the thickness of the carrier made of a membrane so as to accelerate the responding time of the electrode. Then, the enzyme electrode cannot last long, and becomes unstable. In addition, its sensitivity is low.

In an optical process, a reaction product produced by an enzyme reaction is supplied to a flow cell. The substance and a luminescent substance react in the state kept in the flow cell. The fluorescence or chemiluminescence is detected to obtain the quantity of a chemical substance. This optical process has a high detecting sensitivity, but this process can perform only an end assay. Since this process measures the reaction substance by stopping the substance in the flow cell in the same manner as the electrochemical process, the process can measure only in a discrete manner. To stop the reaction substance in the flow cell for this purpose, a three-way valve or the like must be provided in the flow passage. The use of such a valve not only makes the system complex but also may cause problems. In a batch system like this, a pause must be taken after each step of measuring which is a waste of time.

In the chemiluminescence, a pH range adapted for the enzyme reaction and a pH range adapted for the chemiluminescent reaction may differ. In this case, the activity of the enzyme cannot be measured. Therefore, the optical process by the chemiluminescence cannot always be applied to the activity measurements of all enzymes.

SUMMARY OF THE INVENTION

It is an object of the present invention to provide an apparatus for measuring the velocity of an enzyme reaction which is capable of measuring the quantity of a chemical substance in a specimen and the activity of an enzyme in an end assay and a rate assay while a substrate solution is flowing continuously.

According to the present invention, there is provided an apparatus for measuring the velocity of an enzyme reaction wherein chemical substances react in the presence of catalyst of an enzyme. The apparatus comprises a capillary column in which the enzyme is immobilized, and solution supplying means for pumping a solution containing a chemical substance and a luminescent substance in the capillary column. When the solution flows through the column, the enzyme reaction is proceeded by the catalytic action of the enzyme and the reaction product and the luminescent substance react to emit light. Detecting means detects the luminescence in the capillary column to output a signal relative to the distribution of a luminescent intensity along the longitudinal direction of the column. A calculation unit inputting an output signal of the detecting means calculates the enzyme activity or the quantity of the chemical substance from the distribution of the luminescent intensity along the longitudinal direction of the capillary column by an end assay and/or a rate assay.

According to the present invention, the enzyme reaction can be proceeded by the catalytic action of the enzyme immobilized to the capillary column while the solution which contains the chemical substance and the luminescent substance is flowing through the column. An increase in the reaction product in the progress of the enzyme reaction can be detected as an increase in the luminescent intensity in the longitudinal direction of the capillary column. The rate of the increase is calculated to obtain the enzyme activity by the rate assay, and the enzyme activity can be obtained from the luminescent intensity when the rate of the increase is zero by the end assay. Further, since the quantity of the reaction product is optically obtained by the detection of the luminescence, the responding velocity is high, and the accuracy is also high. When the enzyme activity immobilized to the column decreases, the activity of the enzyme can be readily maintained by replacing the capillary column. Still further, with the present invention it is possible to measure the gradation of the quantity of the reaction product while the substance is flowing. Since the substance need not be stopped in the flow cell, the system can be made simple in structure and any pause is unnecessary before each measuring step.

DETAILED DESCRIPTION OF THE PREFERRED EMBODIMENTS

The present invention will now be described in more detail with reference to the accompanying drawings.

Figure 1:
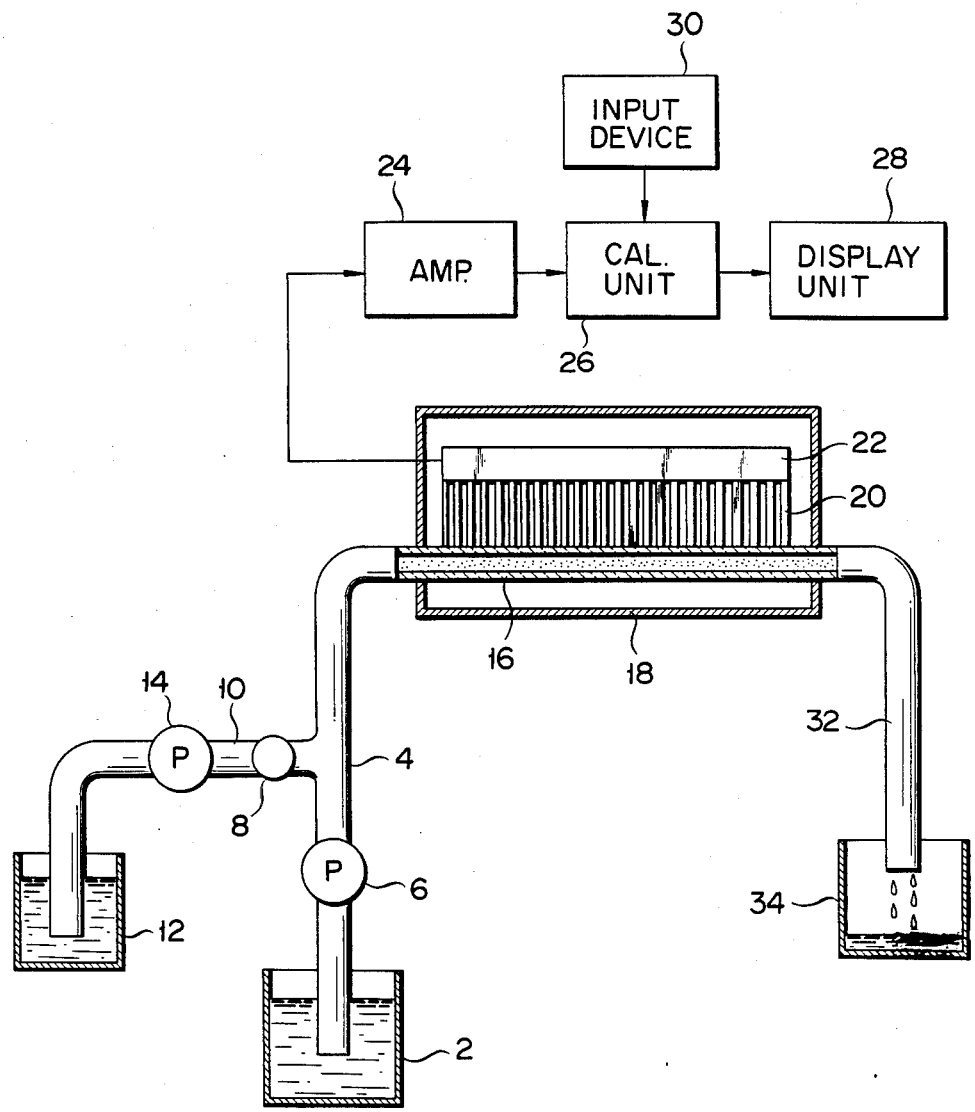
FIG. 1 is a view showing a first embodiment of an apparatus for measuring the velocity of an enzyme reaction according to the present invention.

FIG. 1 shows a first embodiment of an apparatus for measuring the velocity of an enzyme reaction according to the present invention. A substrate solution is contained in vessel 2. One end of conduit 4 formed of fluorine resin and coupled to capillary column 16 is dipped in the substrate solution in vessel 2. Pump 6 is arranged in the course of conduit 4 to supply the solution in vessel 2 to column 16. Conduit 10 is coupled to conduit 4 between column 16 and pump 6, and the other end of conduit 10 is dipped in a sample in vessel 12. Pump 14 is arranged in the course of conduit 10 to add the sample in vessel 12 in the solution flowing through conduit 4. Flowrate control valve 8 is arranged in the course of conduit 10 to regulate the quantity of the sample to be added in the solution.

Capillary column 16 is formed of a material which passes a transparent light, and an enzyme is immobilized in column 16. The sample is added in the substrate solution before the solution is supplied to column 16, and the substrate is mixed with the sample in conduit 4. When the solution containing the luminescent substance flows through column 16, an enzyme reaction is proceeded by the catalyst of the immobilized enzyme, and the reaction product is then reacted with the luminescent substance to emit light. After the reaction is completed, the solution is exhausted through conduit 32 to waste solution vessel 34.

A number of optical fibers 20 are arranged along the longitudinal direction of column 16 so that the photodetecting ends of fibers 20 are directed toward column 16. The photoguide ends of fibers 20 are respectively coupled to the channels of multichannel photodiode array 22. Photodiode array 22 converts the light emitted from column 16 into an electric signal corresponding to the luminescent intensity to output the signal to amplifier 24. The signal from array 22 is amplified by amplifier 24, and then inputted to calculation unit 26. Data such as a velocity of a sample, a type of the sample and a type of the enzyme are inputted from external input device 30 to calculation unit 26. Calculation unit 26 calculates the rate of increase of the luminescent intensity, i.e., the change of the reaction product produced by the enzyme reaction relative to the time on the basis of the data and the luminescent intensity, and calculates the reaction velocity from the gradation of the quantity of the reaction product according to a rate assay. Calculation unit 26 further calculates the end assay of the reaction product when the rate of the increase in the luminescent intensity becomes zero. The enzyme activity obtained by the rate assay and the end assay is displayed on display unit 28. Fibers 20 are provided to prevent a stray light from being incident to array 22. Fibers 20 may not always be necessary when the stray light does not matter. If necessary, a micro channel plate with phosphate plate may be provided in front of the photodiode array.

In the present invention, a luminescent reaction is utilized as enzyme activity detecting means. The enzyme reaction and the luminescent reaction depend upon the pH of the solution, and the state of immobilizing the enzyme is determined in response to the chemical substance to be reacted and a type of enzyme to be used as well as a type of luminescent substance.

The luminescent reaction includes chemiluminescence and bioluminescence.

Substances which are subjected to a chemiluminescent reaction have luminol, lucigenin (bis-N-methylacridinium nitrate), lophine (2,4,5-triphenylimidazole), pyrogallol, siloxane, etc. These substances react with $H_2O_2$ in alkaline property in the presence of iron ion. Therefore, in case of chemiluminescence, oxidase for producing $H_2O_2$ is used for the enzyme reaction.

The oxidases contain glucose oxidase, cholesterol oxidase, pyruvic oxidase, etc. In case, for example, of quantifying the glucose, the glucose oxidase is used as the oxidase. In this case, the glucose is oxidized by the enzyme reaction of the glucose oxidase to product gluconic acid, and $H_2O_2$ produced in this reaction reacts with the luminol to emit light. In the case of chemiluminescence, the luminescent reaction is proceeded with the alkalinity of pH of 10 or higher. However, the enzyme reaction decreases its activity or loses its activity in the alkaline range. In other words, the range that the enzyme stably performs its function is in a neutral range of pH. Thus, there arises a problem that the enzyme reaction and the chemiluminescent reaction have different pH ranges for effectively proceeding the reaction. Therefore, in this case, a process to be described later in necessary.

Chemical substances which emit light in the middle range of pH have bis-(2-4-dinitrophenyl)-oxalate (DNPO) or bis-(2,4-trichlorophenyl) oxalate (TCPO), etc. When these chemiluminescent substances are used, the oxidase is used to produce the $H_2O_2$, and the $H_2O_2$ and the luminescent substance react to emit light.

In this case, when luminol is used as the luminescent substance, iron ion is used for accelerating the luminescence. When the DNPO or TCPO is used as the luminescent substance, porphyrin, fluorosamine or dansyl compound may be used.

Bioluminescence has luciferin luciferase reaction of a firefly and a luciferase reaction of a photobacterium. This luciferin luciferase reaction is practically used as a process for detecting adenosinetriphosphate (ATP). On the other hand, the luciferase reaction of the photobacterium emits light by the reactions of 2 steps as shown in the following chemical reaction formula (See Jeane Ford and Marleue Deluca, Anal. Biochem. 110, 43('83)).

$$H_2 + NAD(P)H + FMN \rightarrow NAD(P)^+ + FMNH_2 \quad (1)$$

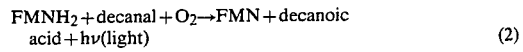

$$FMNH_2 + decanal + O_2 \rightarrow FMN + decanoic\ acid + h\nu(light) \quad (2)$$

where
- NAD(P)H: Reduction type nicotinamide adenine dinucleotide
- FMN: Oxidation type flavin mononucleotide
- NAD(P)+: Oxidation type nicotinamide adenine denucleotide
- FMNH$_2$: Reduction type flavin mononucleotide.

In this case, NADH.FMN oxidoreductase catalyzes the reaction in equation (1), and the luciferase of the photobacterium catalyzes the reaction in equation (2).

The NAD(P) used in the reaction of the first step is a coenzyme of various dehydrogenases. The dehydrogenase removes hydrogen from the substrate, but the NAD(P)+ receives the hydrogen to become NAD(P)H.

Therefore, various substrate and enzyme activity can be detected as luminescent phenomenon in the presence of the dehydrogenase in the bioluminescent reaction. Further, since bioluminescence is proceeded in the middle range of pH, other enzyme reaction may be readily coexisted therewith.

Dehydrogenase contains glucose-6-phosphoric dehydrogenase, lactic dehydrogenase (LDH), malic dehydrogenase (MDH), glutamic dehydrogenase, and 3α-hydroxysteroid dehydrogenase, etc. Dehydrogenases are used with oxidase for analysis of various substances.

Then, a process for immobilizing the enzyme to the capillary column will be described in more detail. When chemiluminescence is utilized, oxidase may be immobilized to capillary column 20. On the other hand, when bioluminescence is utilized, luciferase and NADH.FMN oxidoreductase may be immobilized. In this case, dehydrogenase may also be immobilized, but when luciferase and oxidoreductase are merely immobilized to the capillary column, the column may be commonly used for various dehydrogenase reactions.

Various processes are provided as enzyme immobilizing means. An enzyme solution flows through the capillary column, thereby immobilizing the enzyme to the inner wall of the column. After being immobilized to a carrier such as Dextran, the carrier may be filled in the column. Further, enzyme is immobilized in many pores opened at insoluble fine particles such as glass particles, and, then, a number of glass particles may be filled in the column.

When the enzyme is oxidase such as glucose oxidase, cholesterol oxidase or pyruvic oxidase, etc., the enzyme can stably perform its function in the middle range of pH of 4 to 8. When the luminescent substance has high luminescent intensity in alkaline range such as luminol, it is necessary to immobilize the enzyme as below.

A first process has an binding basic group such as an amino group to the inner wall of a capillary column. Then, oxidase is immobilized in the pores of the porous glass particles, and a number of glass particles, to which the oxidase is thus immobilized, are filled in the column 16. Thus, the stable range of the oxidase may be shifted to the alkaline side. Therefore, when the substrate solution which contains luminescent substance such as luminol flows through the column, the enzyme reaction is proceeded in the alkaline range, and $H_2O_2$ produced by this enzyme reaction reacts with the luminol to emit light.

A second process is used in case of supplying a substrate solution having 9 or higher of pH to a capillary column. In this process, an acidic group such as a carboxylic group is bound to the inner wall of the column. Further, the oxidase is immobilized to the inner wall of the column. Then, since the basic substrate solution is shifted to pH of neutral range by the acidic group introduced to the inner wall in the vicinity of the inner wall, the enzyme reaction occurs in the presence of the oxidase as a catalyst in the vicinity of the inner wall of the column, and $H_2O_2$ produced by the reaction and luminol react at the position except the vicinity of the inner wall to emit light.

A third process is used in case of a substrate solution having 9 or higher of pH. The acidic group such as the carboxylic group is bound to the pores of porous glass particles, and the oxidase is further immobilized to the pores. Then, the glass particles are filled in the column. When the basic substrate solution flows through the column, the vicinity of the glass particles is shifted by the acidic group to a neutral range. Then, the enzyme reaction is proceeded by the oxidase in this portion. $H_2O_2$ produced by the enzyme reaction reacts with the luminol in the solution at the position except the vicinity of the glass particles to emit light.

On the other hand, when the DNPO or TNPO which emits light in a neutral range is used or when bioluminescent substance is used, as the luminescent substance, this consideration is unnecessary in case of immobilizing the enzyme. The enzyme may be merely immobilized to the inner wall of the capillary column.

Then, the operation of the apparatus thus constructed as described above will be described. For instance, bioluminescence utilized to measure the activity of lactic dehydrogenase will be described. Luciferase of photobacterium and NADH.FMN oxidoreductase were immobilized to capillary column 16, a substrate solution in vessel 2 was supplied by pump 6 to column 16, and a sample in vessel 12 is added to the substrate solution. The substrate solution and the sample are mixed in conduit 4, and flows through column 16. The substrate solution contained, for example, FMN, decanal and NAD necessary for luminescence, and the sample was LDH.

The reaction represented by the following formula (3) was proceeded by the action of the LDH to produce NADH.

Lactic acid + NAD → pyruvic acid + NADH       (3)

This reaction started when the substrate solution in conduit 4 was added to the sample. The produced NADH was reacted with the FMN by the catalytic action of the NADH.FMN oxidoreductase immobilized to the column by the reaction represented by formula (1) described above. The produced $FMNH_2$ react with the decanal by the catalytic reaction of the luciferase of photobacterium immobilized to column 16 by the reaction represented by formula (2) described above to emit light.

Figure 2:
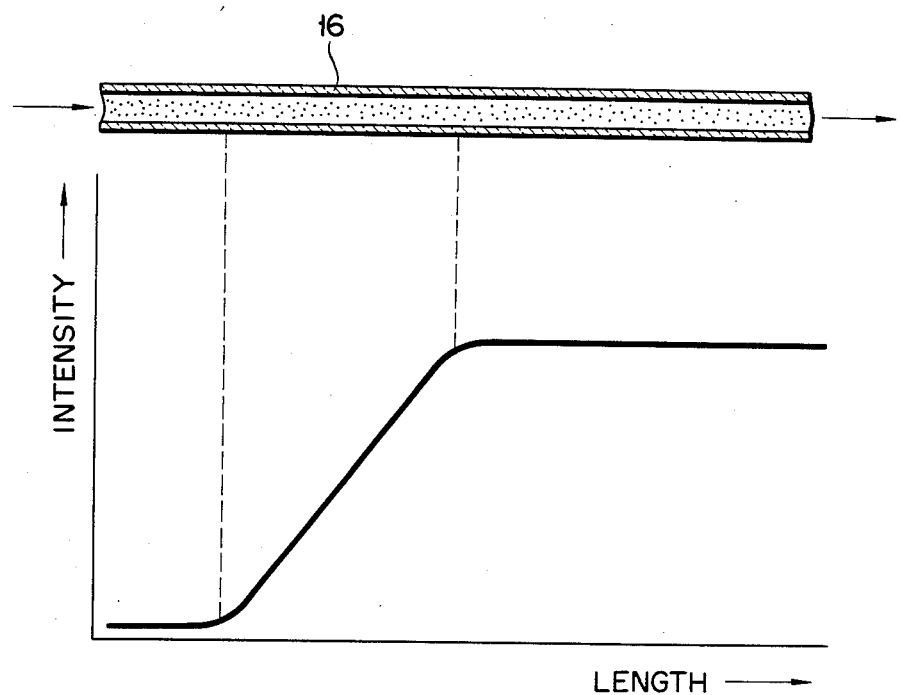
FIG. 2 is a diagram showing the end assay gradient of the reaction product.

This luminescence is detected by photodiode array 22 through fibers 20. Since the enzyme reaction and the luminescent reaction proceed while the solution is flowing through column 16, the detected luminescent intensity increases, as shown in FIG. 2, toward the longitudinal direction of column 16 and finally becomes constant. Calculation unit 26 calculates the rate of increase in the luminescent intensity toward the longitudinal direction of column 16 from the luminescent intensity detected by array 22 (FIG. 2) to obtain the gradient of the quantity of the reaction product. The rate assay is obtained by the gradient of the quantity, and is outputted to display unit 28. The analyzed result is obtained in the end assay from the luminescent intensity when the rate of the increase in the luminescent intensity becomes zero, and is also outputted to display unit 28. Thus, the mixture solution of the substrate solution and the sample flows through the column, and the quantification of the reaction product and the activity of the enzyme can be measured by the end assay and the rate assay.

Then, examples of the present invention will be described. In the first example, a reaction velocity was obtained by utilizing bioluminescence. Luciferase of photobacterium and NADH.FMN oxidoreductase were immobilized to bromided cyan activated Sephrose (Trade name: Pharmacia) by a process of Jean Ford et al (See Jean Ford and Marlene Deluca: Anal Biochem, 110, 43–48 (1983)). This immobilized enzyme composition (hereinbelow referred to as "gel") was filled in a capillary column formed of quartz having 1 mm of inner diameter. Mesh filter was set in both ends of the column so as to prevent the gel from leaking.

Figure 3:
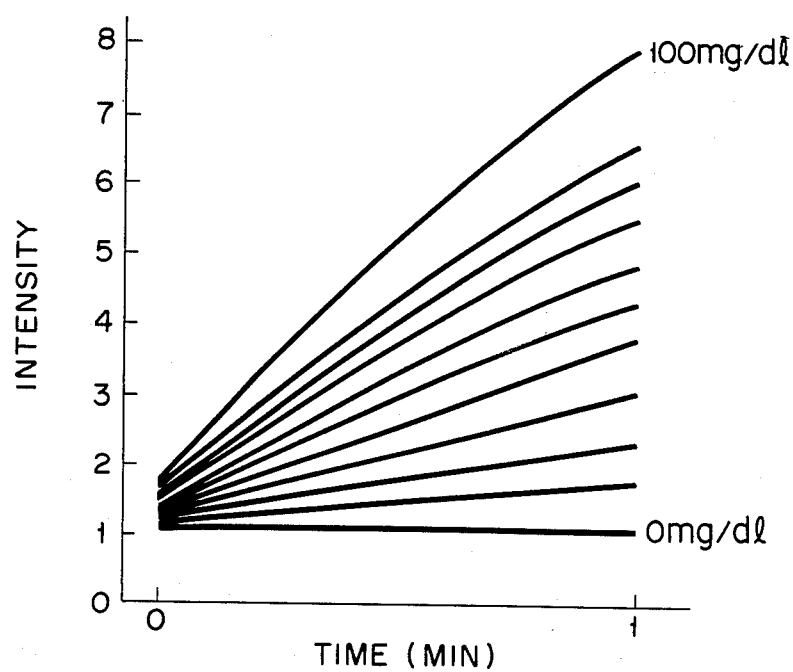
FIGS. 3 and 4 are graphs showing the measured results of the examples of the invention.

In this example, glucose was quantified. The substrate solution, 0.1 mol of phosphoric acid buffer solution (7.5 of pH) which contained 2 m mol of ATP (adenosine-5'-triphosphate), 2 m mol of NADP, 3 μmol of FMN, 5 ppm of decanal, 600 U/l of hexonase and 300 U/l of glucose-6-phosphoric dehydrogenase was used as the substrate solution. The flowing velocity was 0.1 ml/min, and the temperature of a constant temperature bath 18 was 37° C. 0 to 100 mg/dl of glucose solution was used as the sample, and 2 μl of the sample was added to the reaction system. As a result, it could be measured with sufficient sensitivity, as shown in FIG. 3.

Figure 4:
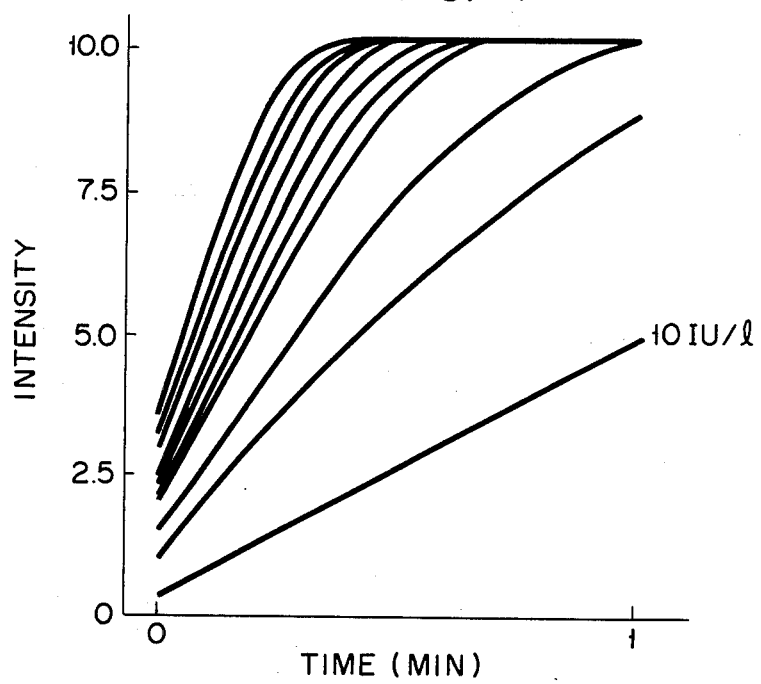

In the second example, LDH was measured. 0.1 mol tribuffer solution (8.5 of pH) which contained 200 m mol of lithium lactate, 2 m mol of NAD, 3 μmol of FMN, and 5 ppm of decanal was used as the substrate solution. The LDH was prepared to become 10 to 100 IU/l, and 2 μl of the LDH was added to the reaction system. The measured result of the luminescent intensity of this case is shown in FIG. 4, and it could be detected similarly with sufficient sensitivity.

Figure 5:
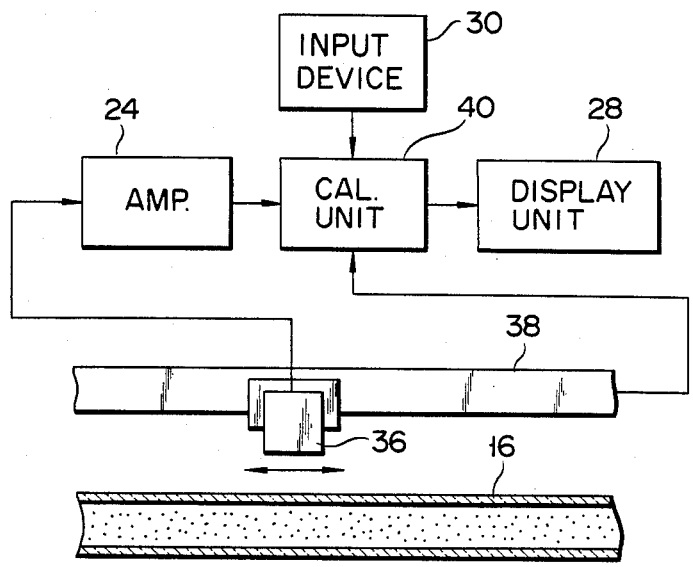
FIGS. 5 and 6 are views showing second and third embodiments of an apparatus according to the present invention.

Then, another embodiment of an apparatus for measuring the velocity of an enzyme reaction according to the present invention will now be described. FIG. 5 shows a second embodiment of the apparatus of the present invention. FIG. 5 shows the vicinity of capillary column 16, and the other construction is similar to that of the first embodiment shown in FIG. 1. In this second embodiment, photodiode (or photomultiplier) 36 is used instead of photodiode array 22. Photodiode 36 is scanned longitudinally of capillary column 16 by drive mechanism 38. In other words, photodiode 36 can be moved along the longitudinal direction of column 16 in the state that the light detecting direction is directed toward column 16. A detection signal of photodiode 36 is inputted through amplifier 24 to calculation unit 40. A signal representing the scanning position of photodiode 36 is also inputted from drive mechanism 38 to calculation unit 40. Unit 40 calculates the enzyme activity by the end assay and the rate assay from the photodetection signal of photodiode 36 and the position signal of drive mechanism 38 in the same manner as the first embodiment, and outputs the result to display unit 28. Various data are inputted from input device 30 to unit 40. Further, in the embodiment described above, column 16 may be scanned longitudinally instead of scanning photodiode 36.

Figure 6:
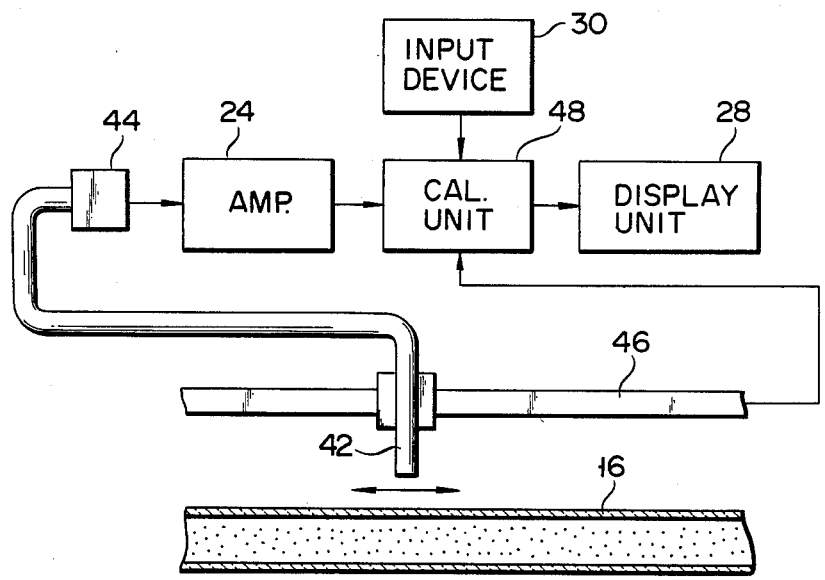

FIG. 6 shows a third embodiment of the apparatus according to the present invention. In this embodiment, it is different from the first embodiment (FIG. 1) that optical fiber 42 and photodiode (or photomultiplier) 44 are used instead of fibers 20 and photodiode array 22 of the first embodiment (FIG. 1). The same reference numerals as in the first embodiment denote the same parts in the third embodiment, and the detailed description thereof will be omitted. Fiber 42 is arranged at the photodetecting end toward capillary column 16. Fiber 42 is scanned by drive mechanism 46 along the longitudinal direction of column 16 in the state that the photodetecting end is directed toward column 16. Fiber 42 is coupled to photodiode 44, and the luminescence in column 16 is converted by photodiode 44 into an electric signal. The detection signal of photodiode 44 is inputted through amplifier 24 to calculation unit 48. A signal representing the scanning position of fiber 42 is inputted from drive mechanism 46 to calculation unit 48, and unit 48 calculates the enzyme activity by the end assay and the rate assay from the photodetection signal and the scanning position in the same manner as the first embodiment, and displays the result on display unit 28.

What is claimed is:

1. An apparatus for measuring the velocity of an enzyme reaction wherein chemical substances react in the presence of catalyst of an enzyme comprising:
   a capillary column in which the enzyme is immobilized;
   solution supplying means for pumping a solution containing chemical substances and a luminescent substance in the capillary column in which, when the solution flows through the column, the enzyme reaction is proceeded by the catalytic action of the enzyme and the reaction product and the luminescent substance react to emit light;
   detecting means for detecting the luminescence in the capillary column to output a signal relative to the distribution of a luminescent intensity along the longitudinal direction of the column; and
   a calculation unit inputting an output signal of the detecting means for calculating the enzyme activity or the quantity of the chemical substances from the distribution of the luminescent intensity along the longitudinal direction of the capillary column by an end assay and/or a rate assay.

2. An apparatus according to claim 1, wherein said detecting means comprises a photodiode array arranged along the longitudinal direction of the capillary column, thereby detecting the distribution of a luminescent intensity along the longitudinal direction of the capillary column.

3. An apparatus according to claim 2, wherein said detecting means comprises a plurality of optical fibers arranged between the photodiode array and the capillary column and arranged along the longitudinal direction of the capillary column, and luminescence in the capillary column is incident through the optical fibers into the photodiode array.

4. An apparatus according to claim 3, wherein said solution supplying means comprises a conduit coupled to one end of the capillary column, a vessel for containing the solution, the other end of the conduit being dipped in the solution, and a pump for supplying the solution to the capillary column.

5. An apparatus according to claim 1, wherein said detecting means comprises a photodiode or a photomultiplier for detecting the luminescence in the capillary column, and a drive mechanism for scanning the photodiode or the photomultiplier in the longitudinal direction of the capillary column, and said detecting means outputs a signal representing the position of the photodiode or the photomultiplier by the drive mechanism and a photodetection signal by the photodiode or the photomultiplier to the calculation unit.

6. An apparatus according to claim 1, wherein said detecting means comprises a photodiode or a photomultiplier, an optical fiber coupled to the photodiode or the photomultiplier, and a drive mechanism for scanning the optical fiber along the longitudinal direction of the capillary column, and said detecting means outputs a signal representing the scanning position of the fiber by the drive mechanism and a photodetection signal by the photodiode or the photomultiplier to the calculation unit.

7. An apparatus according to claim 1, wherein the basic group is bound to the inner wall of the capillary column, oxidase is immobilized to insoluble particles, and the particles are filled in the capillary column to immobilize the enzyme to the column, thereby shifting the stable range of the enzyme to an alkaline side.

8. An apparatus according to claim 1, wherein the acidic group is bound to the inner wall of the capillary column, oxidase is immobilized to the inner wall of the capillary column, and the alkaline solution flows through the column, thereby shifting the vicinity of the inner wall of the capillary column to neutral.

9. An apparatus according to claim 1, wherein the acidic group is bound to insoluble particles, oxidase is immobilized, and the alkaline solution flows through the capillary column, thereby shifting the vicinity of the insoluble particles to neutral.

10. An apparatus according to claim 1, wherein the luminescent substance is a chemiluminescent substance.

11. An apparatus according to claim 1, wherein the luminescent substance is a bioluminescent substance.

* * * * *